United States Patent
Fargahi

(10) Patent No.: US 9,149,380 B2
(45) Date of Patent: Oct. 6, 2015

(54) RELEASE DEVICE FOR DISENGAGING A MEDICAL IMPLANT FROM A CATHETER AND CATHETER HAVING A RELEASE DEVICE

(75) Inventor: Amir Fargahi, Buelach (CH)

(73) Assignee: BIOTRONIK AG, Buelach (CH)

( * ) Notice: Subject to any disclaimer, the term of this patent is extended or adjusted under 35 U.S.C. 154(b) by 441 days.

(21) Appl. No.: 13/614,089

(22) Filed: Sep. 13, 2012

(65) Prior Publication Data

US 2013/0079757 A1    Mar. 28, 2013

Related U.S. Application Data

(60) Provisional application No. 61/538,157, filed on Sep. 23, 2011.

(51) Int. Cl.
*A61F 2/06* (2013.01)
*A61F 2/95* (2013.01)
*A61F 2/24* (2006.01)

(52) U.S. Cl.
CPC ............... *A61F 2/95* (2013.01); *A61F 2/2427* (2013.01); *A61F 2002/9517* (2013.01)

(58) Field of Classification Search
None
See application file for complete search history.

(56) References Cited

U.S. PATENT DOCUMENTS

| | | | |
|---|---|---|---|
| 2002/0111666 A1* | 8/2002 | Hart et al. | ..... 623/1.11 |
| 2005/0080476 A1 | 4/2005 | Gunderson et al. | |
| 2007/0118201 A1 | 5/2007 | Pappas et al. | |
| 2007/0168014 A1 | 7/2007 | Jimenez et al. | |
| 2008/0208209 A1 | 8/2008 | Fischer et al. | |

FOREIGN PATENT DOCUMENTS

EP    1964532 A2    9/2008

OTHER PUBLICATIONS

European Search Report for 12180874.5.

* cited by examiner

*Primary Examiner* — Gregory Anderson
*Assistant Examiner* — Robert Lynch
(74) *Attorney, Agent, or Firm* — Wagenknecht IP Law Group PC

(57) ABSTRACT

A release device for disengaging a medical implant from an insertion device, in which the implant is releasable by a relative movement between a first insertion element and a second insertion element, comprising a body having a proximal end, which faces toward a user in the usage state, and a distal end, which is remote from the user in the usage state, a toothed rack having a first speed range and a second speed range being provided between the proximal end and the distal end, the toothed rack being provided to generate a targeted relative movement between the first insertion element and the second insertion element of the insertion device. Furthermore, the invention relates to an insertion device having such a release device.

16 Claims, 2 Drawing Sheets

RELEASE DEVICE FOR DISENGAGING A MEDICAL IMPLANT FROM A CATHETER AND CATHETER HAVING A RELEASE DEVICE

CROSS REFERENCE TO RELATED APPLICATIONS

This invention claims benefit of priority to U.S. provisional patent application Ser. No. 61/538,157 filed Sep. 23, 2011. The contents of which are herein incorporated by reference in their entirety.

TECHNICAL FIELD

The invention relates to a release device for disengaging a medical implant from a catheter as well as a catheter having a release device for releasing a medical implant for implantation in an animal and/or human body according to the preambles of the independent patent claims.

BACKGROUND

Implants are frequently used in medicine, which must be introduced permanently or at least for a long period of time into an animal and/or human body to fulfill replacement functions. For example, cardiac pacemakers, brain pacemakers for Parkinson patients, cardiac implants, cochlear implants, retinal implants, dental implants, implants for joint replacement, vascular prostheses, or stents are to be mentioned here Implants are connected to catheters for insertion into the body and must be able to be precisely placed and released in a defined manner at the usage location. For this purpose, releasing the implant through a pushing movement is known, for example.

SUMMARY

The invention is based on the object of specifying a release device, using which high-precision and targeted release of an implant can be performed.

A further object can be considered that of providing a corresponding insertion device.

The object is achieved according to the invention by the features of the independent claims. Favorable embodiments and advantages of the invention result from the further claims and to the description.

A release device for disengaging a medical implant from an insertion device is proposed, in which the implant is releasable by a relative movement between a first insertion element and a second insertion element. The release device comprises a body having a proximal end, which faces toward a user in the usage state, and a distal end, which is remote from the user in the usage state, a toothed rack having a first speed range and a second speed range being provided between the proximal end and the distal end, and the toothed rack being provided to generate a targeted relative movement between the first insertion element and the second insertion element of the insertion device.

A simple change from rapid to slow release and vice versa can advantageously be performed. Mechanisms for rapid to slow release are provided for this purpose. The invention allows simple handling, in particular a changeover between the speed ranges. This allows an uncomplicated, easy, and rapid speed regulation during the release of the implant. The release of the implant becomes more precise and rapid.

According to an advantageous embodiment, the first speed range and the second speed range can each be situated along a longitudinal extension of the toothed rack. The first speed range and the second speed range can advantageously be situated on opposing regions of the toothed rack. This allows a compact and simple design of the release device.

According to an advantageous embodiment, an action element can be assigned in each case to the respective speed range, which cooperates with the respective speed range in order to cause the relative movement between the first insertion element and the second insertion element of the insertion device. In particular, the first speed range and the second speed range can be a row of teeth, the speed ranges advantageously having different tooth intervals from one another. The action element can advantageously comprise a gear wheel. In the case of a gear wheel drive, the rotational axis of the gear wheel is orthogonal to the displacement direction of the toothed rack. This allows an implementation of two different speed ranges of the release device in a simple manner. The travel path of a toothed rack to drive is calculated according to the mean circumference of the gear ring of the driving gear wheel and its rotational speed. High precision in the positioning of the implant can be achieved by the use of the gear wheels, instead of using pushing and retraction of the insertion elements as in the prior art. A stable design having two axes instead results.

According to an advantageous embodiment, the action element can be fixed in relation to a housing, which is situated at least around the toothed rack. The housing can particularly form a handle of the insertion device. The action element can preferably be coupled to an actuating element, which protrudes out of the housing. This allows easy and controlled operability of the release device.

According to an advantageous embodiment, the toothed rack can have a feedthrough for one of the insertion elements. This allows a compact arrangement which stabilizes and protects the fed-through insertion element. If the insertion device is a catheter, the relevant insertion element can be an internal shaft of the catheter.

According to a further aspect of the invention, an insertion device for inserting a medical implant is provided, which is releasable by a relative movement between a first insertion element and a second insertion element, comprising a release device for disengaging the medical implant, comprising a body having a proximal end, which faces toward a user in the usage state, and a distal end, which is remote from the user in the usage state, a toothed rack having a first speed range and a second speed range being provided between the proximal end and the distal end, the toothed rack being provided to generate a targeted relative movement between the first insertion element and the second insertion element of the insertion device.

The insertion device can advantageously be a catheter. The insertion device can particularly advantageously be used to install and release a prosthesis, a heart valve, or a stent.

According to an advantageous embodiment, an inner insertion element can be guided by the toothed rack. This allows a compact construction of the insertion device.

According to an advantageous embodiment, the toothed rack can be fixed on the airlock device. The arrangement can be implemented as very stable.

DESCRIPTION OF THE DRAWINGS

The invention is explained in greater detail hereafter for exemplary purposes, on the basis of exemplary embodiments shown in the drawings. In the schematic figures.

DETAILED DESCRIPTION

Figure 1:
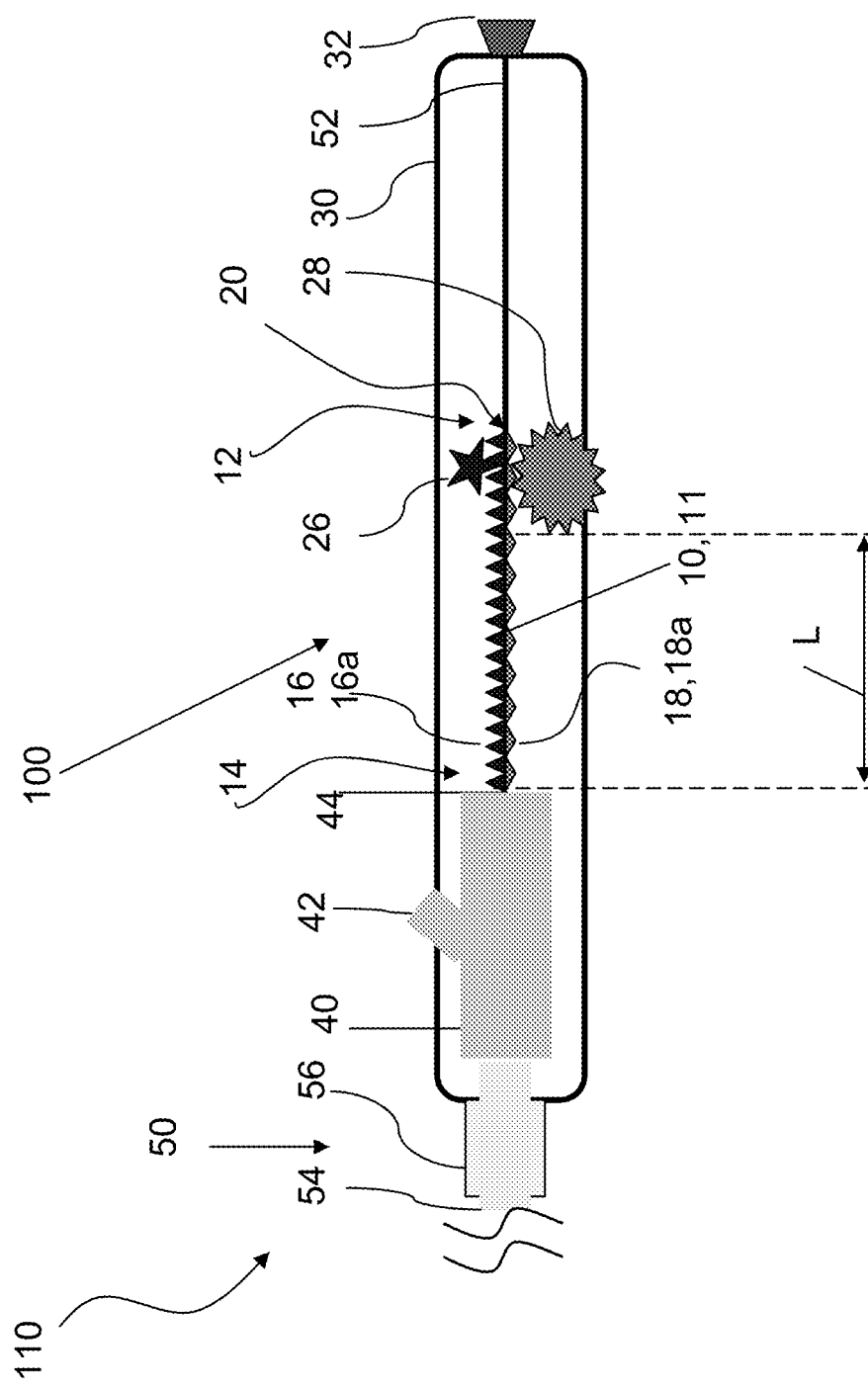
FIG. 1 shows a section through an advantageous exemplary embodiment of an insertion device and a release device.

Functionally identical or identically acting elements are each identified by the same reference numerals in the figures. The figures are schematic illustrations of the invention. They show nonspecific parameters of the invention. Furthermore, the figures solely reproduce typical embodiments of the invention and are not to restrict the invention to the illustrated embodiments.

Figure 2:
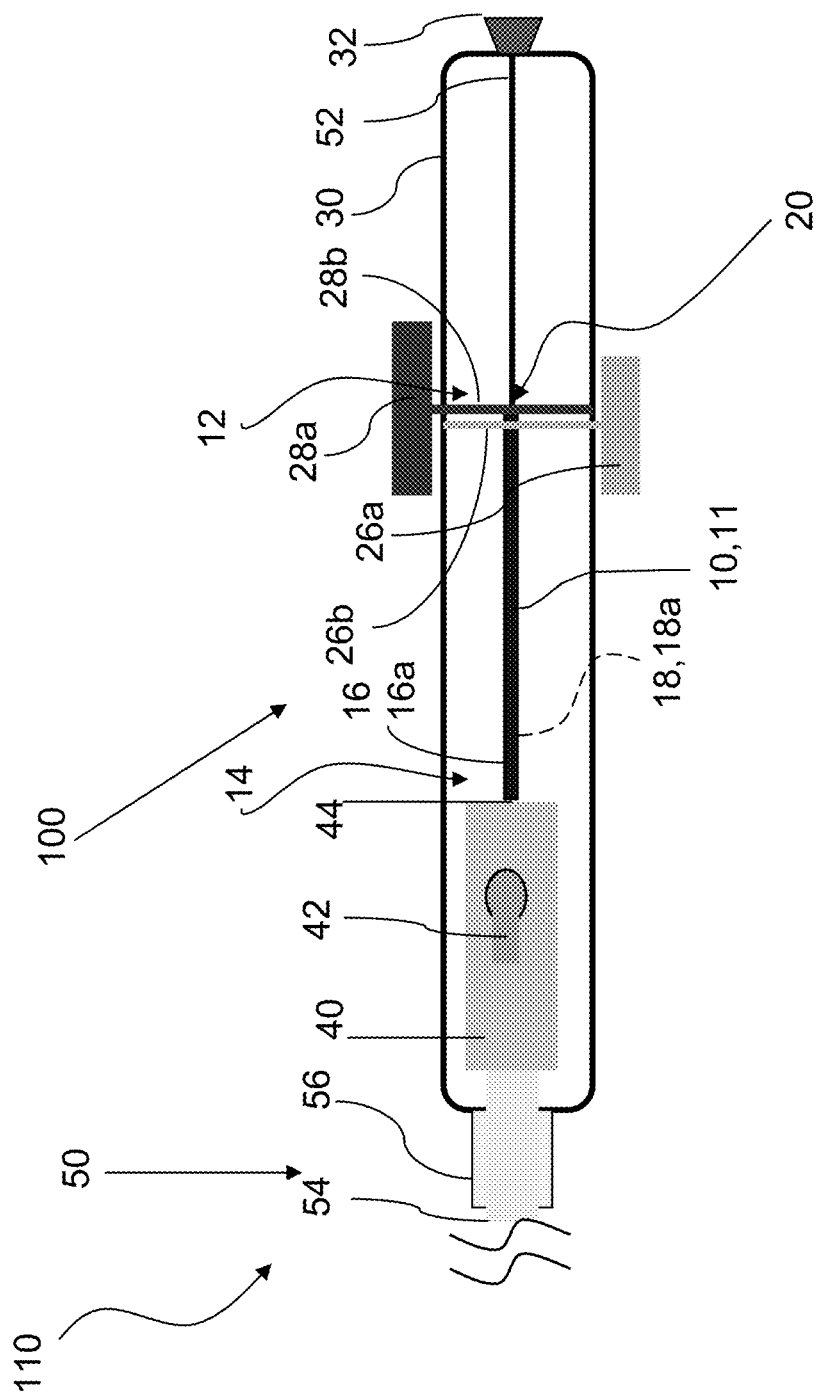
FIG. 2 shows a top view of the insertion device and release device from FIG. 1.

FIG. 1 shows a longitudinal section through an advantageous exemplary embodiment of a release device 100 of an insertion device 110 (only partially shown). The release device 100 is used to disengage a medical implant (not shown) from the insertion device 110, the implant being releasable by a relative movement between a first insertion element and a second insertion element 52, 54. FIG. 2 shows a top view thereof.

The insertion device 110 is, for example, a catheter having a shaft region 50 having an inner shaft 52 and an outer shaft 54 enclosing it, which can in turn be enclosed by an outer envelope 56. The insertion device is only shown at its proximal end, which faces toward a user. The implant (not shown) is typically placed at the distal end of the shaft region 50 between inner shaft and outer shaft and is to be released at the implantation location in the animal or human body.

The release device comprises a body 10 having a proximal end 12, which faces toward the user in the usage state, and a distal end 14, which is remote from the user in the usage state. A toothed rack 11 having a first speed range 16 and a second speed range 18 is provided between the proximal end and the distal end 12, 14. The toothed rack 11 is used to generate a targeted relative movement between the first insertion element and the second insertion element 52, 54 of the insertion device. The speed ranges 16, 18 are implemented as rows of teeth 16a, 18a having different tooth intervals, which are each situated along a longitudinal extension L on opposing sides of the toothed rack 11.

One action element 26, 28 in the form of a gear wheel is assigned in each case to the respective speed range 16, 18, which cooperates with the teeth of the respective speed range 16, 18 in order to cause a relative movement between the first insertion element and the second insertion element 52, 54 to release the implant from the insertion device 110. The first speed range 16 has a row of teeth 16a with closely-spaced teeth, which causes a slow movement during rotation of the gear wheel 26. The second speed range 18 has a row of teeth 18a having wider tooth intervals, which causes a rapid movement during rotation of the gear wheel 28.

The two action elements 26, 28 are fixed in relation to a housing 30, which encloses the toothed rack 11 or the body 10, so that during rotation of the gear wheels, the toothed rack slides over one insertion element 52, i.e., the inner shaft of the catheter, for example. The toothed rack 11 has a feedthrough 20 for the insertion element 52 for this purpose.

The travel path s of the toothed rack 11 results from the mean circumference U of the gear ring ($U=\pi \times d$; where d=mean diameter) of the driving gear wheel 26 or 28 and the rotational speed n of the gear wheel 26 or 28 where $s=U \times n$.

The lumen of the insertion element 52 (inner shaft) can be deaerated and/or flushed using a deaeration valve 32 (also known as a Luer lock).

The toothed rack 11 is fixed at its distal end 14 on an airlock device 40 on a fixation 44. The airlock device 40 can be a so-called T body. The airlock device 40 has a deaeration valve 42 (also known as a Luer lock), through which air can be removed from the lumen of the insertion elements 52, 54 or from the intermediate space between them and a liquid can be introduced, for example. The airlock device 50 is connected to an outer of the insertion elements 54, i.e., to the outer shaft of the catheter, for example, and optionally to a protective envelope 56 around the insertion element 54.

The action elements 26, 28 are coupled by actuating elements 26a, 28b protruding out of the housing 30, so that the respective gear wheel 26, 28 can be comfortably externally actuated.

The actuating elements 26a, 28a are each connected using a shaft 26b, 28b to the respective action element 26, 28, so that the axis of the action elements 26, 28 is perpendicular to the movement direction of the toothed rack 11.

The actuating elements 26a and 28a allow a rapid change from a slow movement (using actuating element 26a) to a rapid movement (actuating element 28a) and vice versa, in that the grip can be changed from one actuating element 26a or 28a to the other 28a or 26a and therefore the respective gear wheel (action element 26 or action element 28) is rotated or stopped.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A release device for disengaging a medical implant from an insertion device, in which the implant is releasable by a relative movement between a first insertion element and a second insertion element, comprising a body having a proximal end, which faces toward a user in the usage state, and a distal end, which is remote from the user in the usage state, wherein a toothed rack having a first speed range and a second speed range is provided between the proximal end and the distal end, and the toothed rack is provided to generate a targeted relative movement between the first insertion element and the second insertion element of the insertion device.

2. The release device according to claim 1, wherein the first speed range and the second speed range are each situated along a longitudinal extension of the toothed rack.

3. The release device according to claim 1, wherein the first speed range and the second speed range are situated on opposing regions of the toothed rack.

4. The release device according to claim 1, wherein the first speed range and the second speed range are rows of teeth, and the speed ranges have different tooth intervals from one another.

5. The release device according to claim 1, wherein the toothed rack has a feedthrough for one of the insertion elements.

6. The release device according to claim 1, wherein an action element is assigned in each case to the respective speed range, which cooperates with the respective speed range in order to cause the relative movement between the first insertion element and the second insertion element of the insertion device.

7. The release device according to claim 6, wherein the action element comprises a gear wheel.

8. The release device according to claim 6, wherein the action element is fixed in relation to a housing, which is situated at least around the toothed rack.

9. The release device according to claim 8, wherein the first insertion element has a deaeration valve.

10. The release device according to claim 8, wherein the action element is coupled to an actuating element, which protrudes out of the housing.

11. A catheter for inserting a medical implant, configured with the release device according to claim 10, wherein the catheter further comprises an inner shaft enclosed by an outer shaft, wherein both shafts extend distally from the housing, further wherein the medical implant is placed at the distal end of the shaft region between inner shaft and outer shaft.

12. The catheter according to claim 11, wherein the toothed rack has a feedthrough for the inner shaft of the catheter.

13. The catheter according to claim 11, wherein actuation of the release device causes the relative movement between the inner shaft and the outer shaft of the catheter.

14. The insertion device according to claim 11, wherein the action element is a gear wheel, which can be actuated by an actuating element and which protrudes out of a housing, further wherein the gear wheel is situated at least around the toothed rack.

15. The catheter according to claim 11, wherein an airlock device is connected at its distal end to the proximal end of the outer shaft of the catheter, wherein the airlock device is situated within the distal end of the housing.

16. The catheter according to claim 15, wherein the toothed rack is fixed on its distal end to the proximal end of the airlock device on a fixation within the housing.

* * * * *